United States Patent [19]

Shimono et al.

[11] Patent Number: 5,766,611

[45] Date of Patent: Jun. 16, 1998

[54] COSMETIC PRODUCTS CONTAINING A SOLUBLE GLASS

[75] Inventors: Fujio Shimono; Koichi Yamamoto, both of Nagoya; Toshiyuki Onishi, Ichinomiya; Ryota Miyoshi, Yono, all of Japan

[73] Assignee: Ishizuka Garasu Kabushiki Kaisha, Nagoya, Japan

[21] Appl. No.: 562,493

[22] Filed: Nov. 30, 1995

Related U.S. Application Data

[60] Continuation-in-part of Ser. No. 162,943, Dec. 8, 1993, abandoned, which is a division of Ser. No. 838,692, Feb. 21, 1992, Pat. No. 5,290,544.

[30] Foreign Application Priority Data

Feb. 22, 1991 [JP] Japan ................................ 3-114188

[51] Int. Cl.$^6$ .................................. A61K 7/00; A61K 7/07
[52] U.S. Cl. .................. 424/401; 424/618; 424/630; 424/641; 424/70.1; 514/845
[58] Field of Search ......................... 424/401, 69, 70.1, 424/618, 630, 641; 514/895

[56] References Cited

U.S. PATENT DOCUMENTS 4,906,464  3/1990  Yamamoto ........................ 424/78
4,911,898  3/1990  Hagiwara et al. ................ 423/118

FOREIGN PATENT DOCUMENTS 0174707  8/1989  Japan.

*Primary Examiner*—Sally Gardner-Lane
*Attorney, Agent, or Firm*—Townsend & Banta

[57] ABSTRACT

The cosmetic product comprises soluble glass particles and liquid cosmetic base containing water. The soluble glass contains antibacterial metal ions selected from the group consisting of $Ag^+$, $Cu^+$, $Cu^{2+}$ and $Zn^{2+}$. The antibacterial ions contained are forming a solid solution with the components of soluble glass and elute along with the dissolution of the soluble glass skeletal network. The eluting rate of metallic ions is determined by the dissolving rate of the soluble glass and is not affected by the environmental concentration of alkaline metal ions, such as $Na^+$.

19 Claims, 4 Drawing Sheets

FIG. 1 soluble glass particle

● Ag⁺ ion (antibacterial ion)

○ Other ions consisting the network of soluble glass

FIG. 2 soluble glass particle
shrinking with the
dissolution

● $Ag^+$ ion (antibacterial ion)

○ Other ions consisting the network of soluble glass

FIG. 3A

Surface of Zeolite Particle

Pores

COSMETIC PRODUCTS CONTAINING A SOLUBLE GLASS

CROSS REFERENCE TO A RELATED APPLICATIONS

This is a Continuation-In-Part patent application of application Ser. No. 08/162,943 filed Dec. 8, 1993, now abandoned, which was a divisional application of Ser. No. 8/38,692, filed Feb. 21, 1992 of U.S. Pat. No. 5,290,544 issued Mar. 1, 1994.

FIELD OF THE INVENTION

This invention relates to liquid-based cosmetic products, particularly to those exhibiting excellent antibacterial property due to metal ion-discharge from soluble glass particles contained.

BACKGROUND OF INVENTION

Liquid-based cosmetics, such as skin lotion, shampoo or rinse, are generally used in our daily life and have been mass-produced in factories. These products are directly applied to human skin, so that the manufacturing process has been strictly controlled for preventing bacterial contamination upon the products. However, after unsealing the package for usage, bacteria or mold may intrude into and grow in the cosmetics, so that various antibacterial agent has been added to the cosmetics.

Figure 3A:
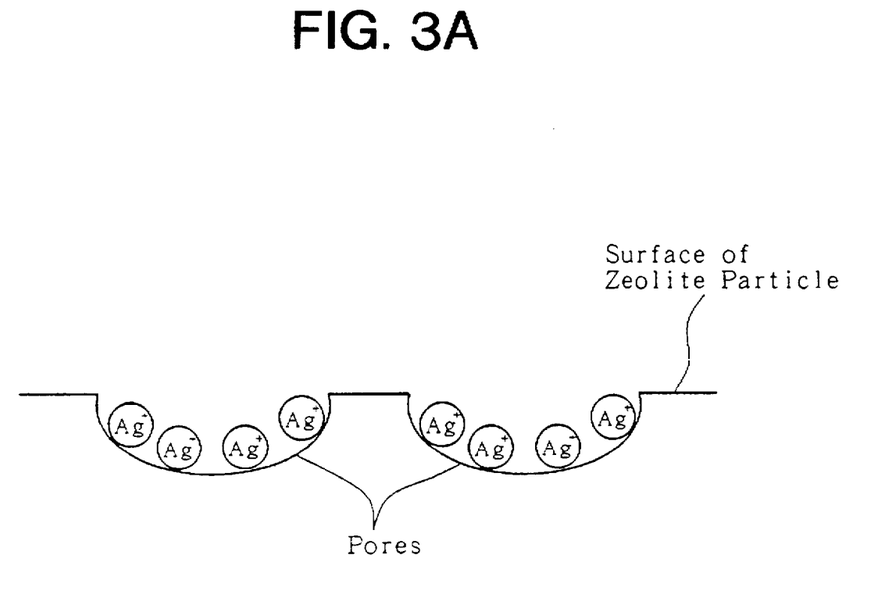
FIG. 3 is a schematic illustration explaining the zeolite particles supporting $Ag^+$ as antibacterial ions in the pores.

Hagiwara et al. (U.S. Pat. No. 4,911,898) and Yamamoto et al. (U.S. Pat. No. 4,906,464) proposed liquid cosmetic products containing zeolite-based inorganic antibacterial agent. In these cosmetics, fine zeolite particles supporting antibacterial metal ions, such as $Ag^+$, $Cu^+$ or $Cu^{2+}$, $Zn^{2+}$ and so on (represented by $Ag^+$, hereinafter), are blended as an antibacterial agent. The $Ag^+$ ions are adsorbed in the pores of the particles as conceptually illustrated in FIG. 3(a), and discharged therefrom due to a chemical ion-exchange reaction between the alkaline metal ions, such as $Na^+$ or $K^+$ (represented by $Na^+$, hereinafter), in the liquid cosmetic base. The discharged $Ag^+$ ions are to exhibit antibacterial property.

Figure 4A:
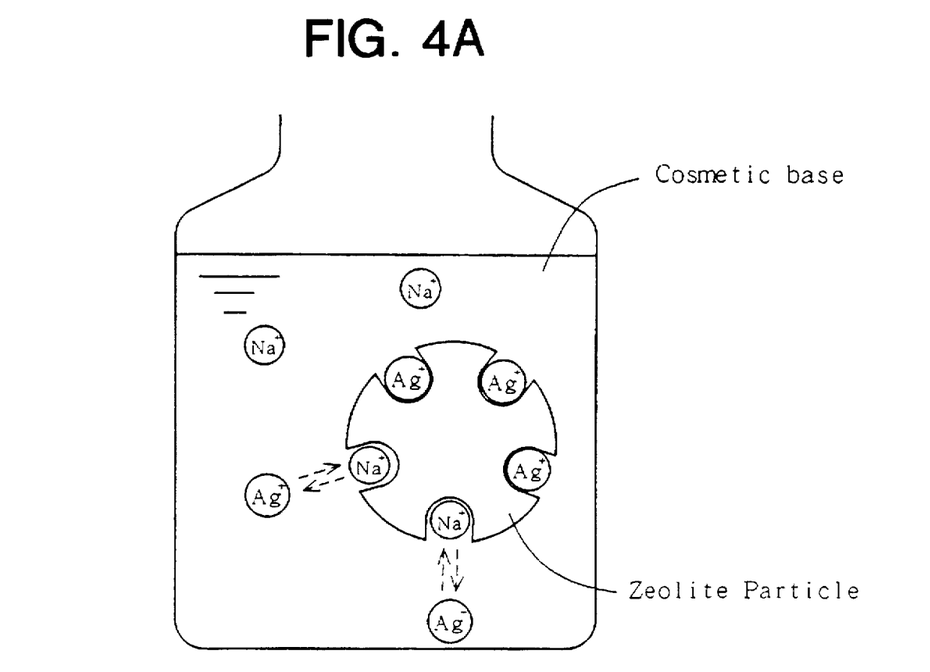
FIG. 4 is a schematic illustration explaining the mechanism of $Ag^+$ ion-discharge from zeolite particles.
Figure 4B:
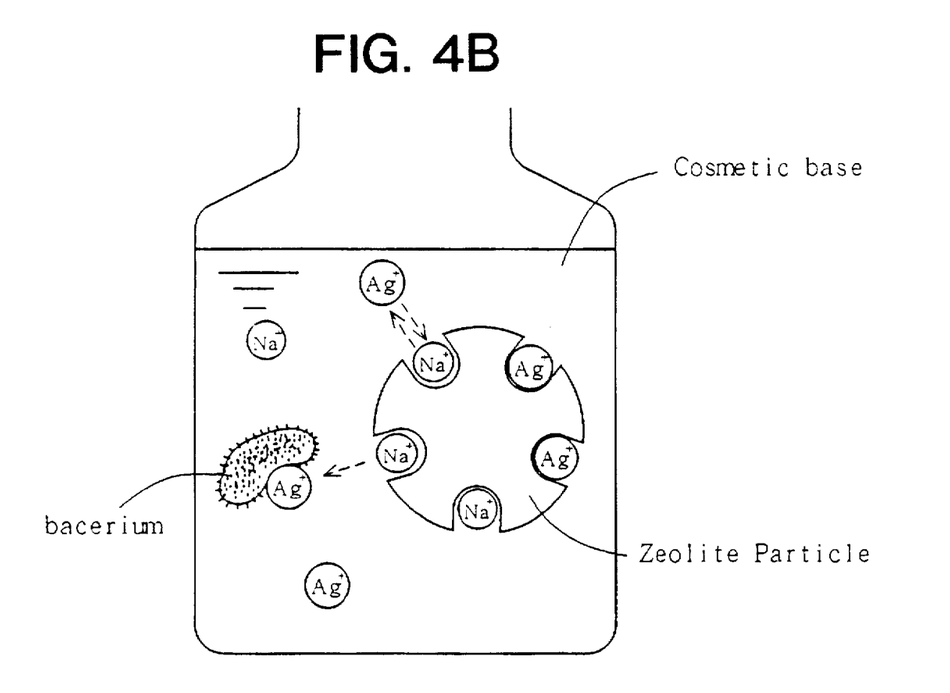

As is shown in FIG. 4(a), the rate of $Ag^+$ ion-discharge is determined by the concentration equilibrium between the $Na^+$ and $Ag^+$ in the cosmetic base. When $Ag^+$ ions are consumed by the sterilization process, said ion-exchange reaction proceeds for keeping the equilibrium as shown in FIG. 4(b). Thus, the cosmetic product is to maintain an almost constant concentration of the discharged $Ag^+$ and its sterilizing ability until all $Ag^+$ ions are consumed.

Because of such $Ag^+$ discharging mechanism, the conventional zeolite-based cosmetics appear to have following disadvantages.

(1) The rate of $Ag^+$ ion-discharge from the zeolite particle is determined by said concentration equilibrium and greatly influenced by the environmental ion concentration. $Ag^+$ discharging rate is to be controlled only by an adjustment of the $Na^+$ concentration in the cosmetic base. $Na^+$ ions are, however, added in a form of an alkaline component, and the range of addition is very limited for maintaining a suitable pH value of the cosmetics. In other words, it is substantially impossible to control the $Ag^+$ ion-discharge for such cosmetic products. Therefore, the concentration of Na in the recipe of cosmetics often becomes excess or short for obtaining an optimum ion-discharging rate, thereby causing a lack of duration in the antibacterial effect due to a drastic discharge of $Ag^+$ ions from zeolite particles, or insufficiency of antibacterial effect due to a lack of $Na^+$ for promoting said chemical ion-exchange, respectively. Furthermore, it is difficult to obtain neutral or weak acidic cosmetics since the recipe is to inevitably contain alkaline components as a source of $Na^+$, and the variety of cosmetic products is limited.

Figure 3B:
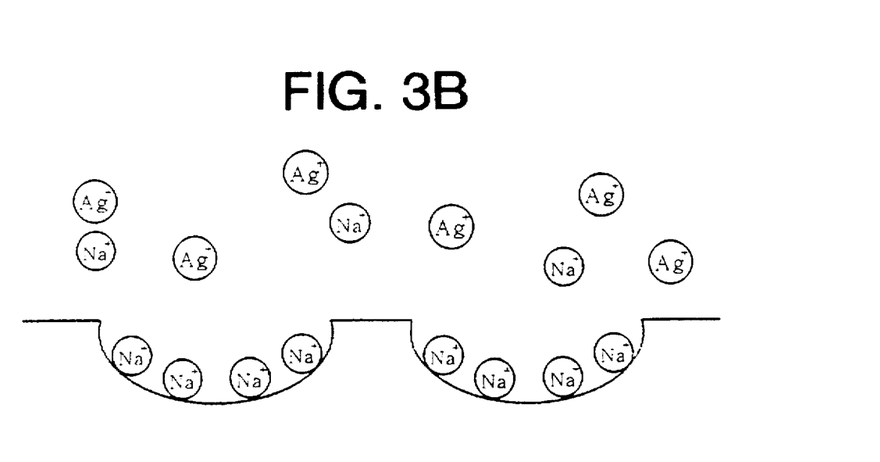

(2) The ion exchange reaction between $Ag^+$ and $Na^+$ may proceed catastrophically on a $Na^+$-rich human skin. In this case, enormous amount of $Ag^+$ ions are to be discharged at once as shown in FIG. 3(b), and considerable part of discharged $Ag^+$ ions may be reduced to metallic Ag particles by exposure to light, thereby causing a phenomenon that the cosmetics applied on the face turn slightly black.

(3) When such zeolite-based cosmetics are preserved under exposure to strong light, the amount of $Ag^+$ ions in the cosmetics decreases since they are extensively reduced to metallic Ag particles. This may shorten the duration of antibacterial effect and cause the color change of cosmetics.

The object of this invention is to offer a cosmetic product containing inorganic antibacterial agent which exhibits excellent duration of antibacterial effect and does not cause catastrophic discharge of metallic ions when it is applied on a human skin.

SUMMARY OF THE INVENTION

For solving the aforementioned object, the cosmetic product relating to this invention comprises soluble glass particles and liquid cosmetic base containing water. The soluble glass contains antibacterial metal ions selected from the group consisting of $Ag^+$, $Cu^+$, $Cu^{2+}$ and $Zn^{2+}$, which elute from said soluble glass particles with the dissolution of said soluble glass into water. In this specification, "antibacterial" is to contain a meaning of destructive to or inhibiting the growth of not only bacteria but also mold or other fungi.

Figure 1:
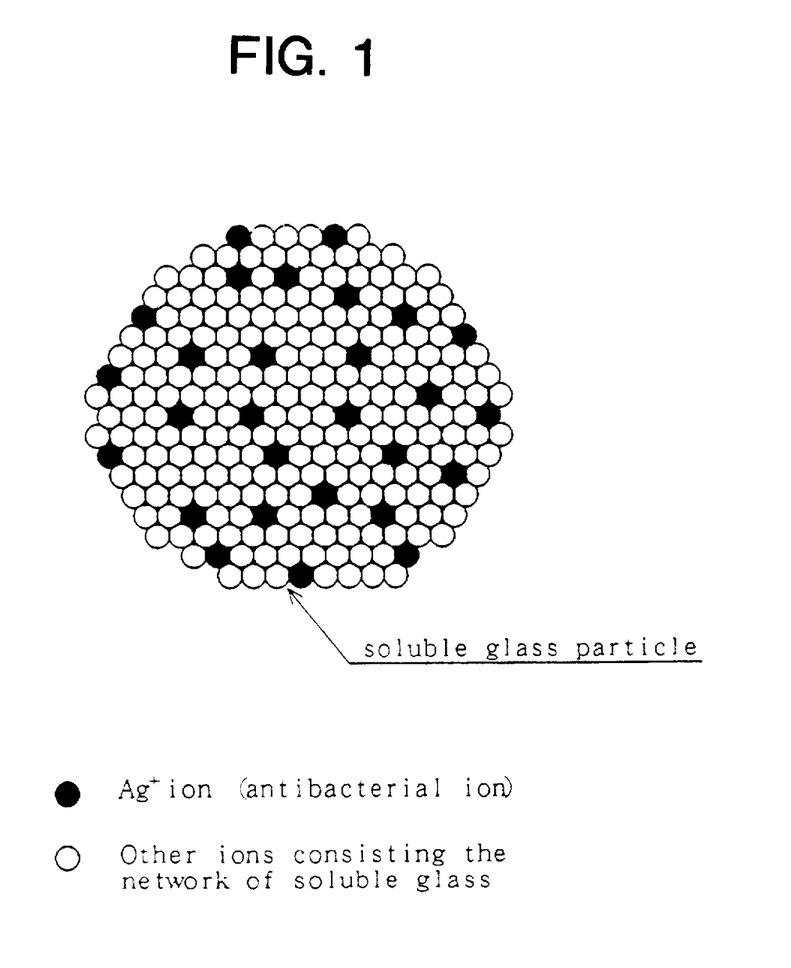
FIG. 1 is a schematic illustration of a soluble glass particle containing $Ag^+$ ions.
Figure 2:
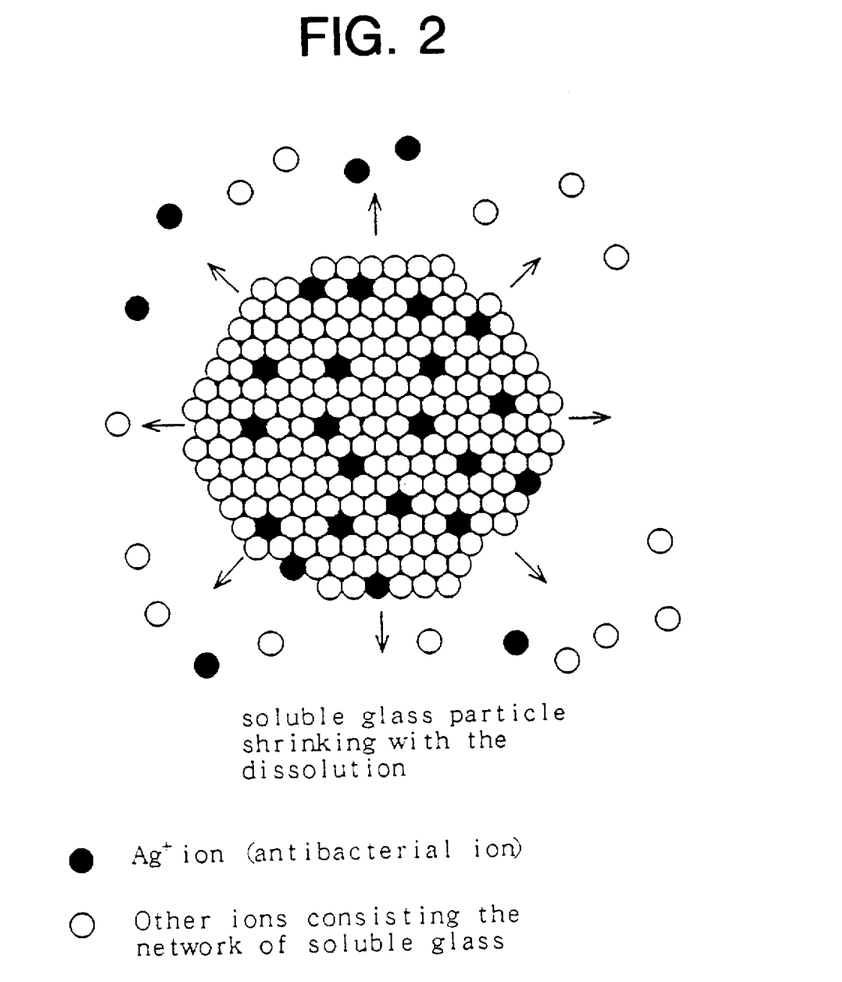
FIG. 2 is a schematic illustration of a soluble glass dissolving into water.

This cosmetic product exhibits an antibacterial property due to metal ions discharged from the soluble glass particles. The ion discharging mechanism thereof is essentially different from that of zeolite particles in the conventional cosmetics. That is to say, the antibacterial metal ions (antibacterial ions, hereinafter) contained are forming a solid solution with the components of soluble glass as schematically illustrated in FIG. 1, and as shown in FIG. 2, the antibacterial ions elute along with the physical dissolution of the soluble glass skeletal network, not due to a chemical ion exchange mechanism. Such mechanism of ion elution brings about the following unique advantages.

(1) It is very easy to control the eluting rate of antibacterial ions by adjusting the size or composition of the soluble glass particle regardless of the environmental concentration of $Na^+$. Therefore, long term duration of antibacterial effect is easily achieved only by setting the size or composition of the soluble glass to a designated value, and the cosmetics can be preserved in a good condition for a long time even after unsealing the package. Furthermore, the addition of alkaline-metal ions, such as $Na^+$, are no longer necessary for maintaining the ion-discharge, so that neutral or weak acidic cosmetics can be easily obtained. Even if an addition of such an alkaline component is required to achieve other purpose (pH value adjustment, for example), the quantity of addition thereof can be chosen in a wide range. Thus, much variety of cosmetics can be realized.

(2) The eluting rate of antibacterial ions from the soluble glass particles are controlled well even on a $Na^+$-rich human skin, since the ions elute due to the physical dissolution of the soluble glass, not due to the chemical ion exchange reaction. Therefore, there is no need to worry about drastic discharge of ions as observed in the conventional zeolite-based cosmetics.

(3) In the case that the antibacterial ions are photosensitive $Ag^+$, the amount of eluted $Ag^+$ ions never decreases drastically during the preservation of the cosmetics under exposure to light, since the decrease in the amount of eluted $Ag^+$ ions due to the photochemical reduction never affects the solubility of the glass particles.

The cosmetic base used in this invention can comprise a liquid material selected from the group consisting of liquid foundation, skin lotion, milky lotion, shampoo, hair rinse and cream. In this case, the cosmetic products preferably contains more than 40 wt % of water in the recipe thereof. When the cosmetic base is a liquid material selected from the group consisting of skin lotion, milky lotion, shampoo and hair rinse, the cosmetic products preferably contain more than 65 wt % of water in the recipe thereof for maintaining a sufficient flowability.

As the soluble glass for this invention, a borosilicate glass or a phosphate glass is preferably used. A conventional sodium glass has a strong three-dimensional skeletal network structure consisting of $Si^{4+}$, $Na^+$ and $O^{2-}$, and the ionic bonding in the network is so strong that the solubility of the conventional glass in water is almost zero. On the other hand, the soluble glass used in this invention is, however, prepared by melting $B_2O_3$ or $P_2O_5$ along with the common raw material of conventional glass. $B_2O_3$ or $P_2O_5$ component weakens the bonding of the network and make the skeletal network itself soluble in water. The net work structure of the glass is weakened with increasing the content of $B_2O_3$ or $P_2O_5$, thereby causing an increase in the solubility of the glass in water. Therefore, adjusting the solubility of the glass by changing the content of $B_2O_3$ or $P_2O_5$ is one of the effective methods for controlling the eluting rate of antibacterial ions from the glass particles.

As the antibacterial ions, $Ag^+$, $Cu^+$ or $Cu^{2+}$ (particularly $Ag^+$) is used preferably. It is traditionally known that a silver or copper vessel for food can prevent rotting of the food. This is due to the fact that a very slight amount of silver or copper ion is eluted from the silver or copper vessel. It is said that about 20 µg/l of silver in a solution indicates a bactericidal action. In general, silver or copper ions in even a very slight amount can exhibit an action what is called "oligodynamic metal effect" to prevent growing of fungi or the like. Such metal ions are capable of being bonded to an activating enzyme center in a cell of bacterium or mold to exhibit a strong bactericidal action.

As the source of $Ag^+$, $Cu^+$ or $Cu^{2+}$, metal oxides such as $Ag_2O$, $Cu_2O$ or $CuO$ are preferably used. These oxides are blended to the starting material of the soluble glass.

The soluble glass used for this invention can be prepared by any method like that of an ordinary glass. For example, a batch of glass material adjusted to a designated composition may be heated to be vitrified. Alternatively, the soluble glass may be manufactured by a sol-gel method. In this method, each oxide as the starting material is prepared as a sol of metal-oxide hydrate, which is obtained by hydrolysis of metallic ions or metal alkoxide. A mixture containing designated amount of each sol is evaporated, and then the objective soluble glass is to be obtained.

Both in the methods mentioned above, the blended metal ions are mixed homogeneously in a molten or liquid state, and the distribution of the metal ions is so uniform all over the particle that the antibacterial effect can endure until the soluble glass particles dissolve up. To the contrary, the zeolite particles used for the conventional cosmetics never dissolve into water, and the metallic ions are supported only on the surface of the particles, so that the supported ions are depleted in a relatively short period, and long term duration of the antibacterial effect cannot be expected.

Then, the soluble glass obtained are pulverized to a designated particle size. More specifically, the cosmetic products of this invention may be manufactured by crushing the soluble glass obtained into beads having an average particle size of about 2–10 mm, adding a desired amount of the beads into a vessel containing water in a recipe of the cosmetic products, and enclosing the beads in the vessel under a condition that the beads always contacts with the water.

As a typical composition of the soluble glass, a borosilicate glass containing $B_2O_3$, $SiO_2$, $Na_2O$ and $Ag_2O$ are preferably used. In this case, the composition should preferably contain 10–30 mol % of $B_2O_3$, 40–60 mol % of $SiO_2$, 20–40 mol % of $Na_2O$ and 0.1–2 wt. % of $Ag_2O$. $B_2O_3$ content less than 10 mol % may cause a crystallization of the material which leads to an insufficiency of the glass solubility, and more than 30 mol % of $B_2O_3$ may cause an excess solubility of the glass and a consolidation of the particles due to a high hygroscopicity of the glass. $SiO_2$ and $Na_2O$ are the fundamental components for maintaining the strength of the skeletal network of the glass, so that the content under the lower limit of the range indicated above may lead to an excess solubility of the glass and the content over the upper limit of the range may cause lack of the glass solubility. On the other hand, less than 0.1 wt % of $Ag_2O$ may cause a lack of the antibacterial effect, and more than 2 wt % of $Ag_2O$ may bring about an excess elution of $Ag^+$ which leads to a color change of the cosmetics due to a generation of metallic Ag particles. It is more preferable that the glass composition contain 15–25 mol % of $B_2O_3$, 45–55 mol % of $SiO_2$, 25–35 mol % of $Na_2O$ and 0.1–2 wt % of $Ag_2O$.

One more typical composition of the soluble glass which can be preferably applied to this invention is a phosphate glass containing $P_2O_5$, at least one of CaO and MgO, $Al_2O_3$ and $Ag_2O$. In this case, the composition should preferably contain 38–58 mol % of $P_2O_5$, 32–52 mol % of at least one of CaO and MgO in total, 6–14 mol % of $Al_2O_3$ and 0.1–2 wt % of $Ag_2O$. The critical meaning of the ranges for $P_2O_5$ and $Ag_2O$ are equivalent to those of $B_2O_3$ and $Ag_2O$ for said borosilicate glass, respectively. Furthermore, the CaO and/or MgO and $Al_2O_3$ function as the network-strengthening component, so that the critical meaning of the indicated content range thereof corresponds to those o the $SiO_2$ and $Na_2O$ for aforementioned borosilicate glass. It s more preferable that the glass composition contains 43–53 mol % of $P_2O_5$, 37–47 mol % of at least one of CaO and MgO in total 8–12 mol % of $Al_2O_3$ and 0.1–2 wt % of $Ag_2O$.

Since the antibacterial ions elutes due to the physical dissolution of the soluble glass, the rate of elution of antibacterial ions from the soluble glass particles can be easily controlled by, for example, adjusting the chemical composition of soluble glass or regulating the size and distribution of the soluble glass particles. Therefore, it is very easy to control the magnitude of antibacterial effect and the duration of the effect corresponding to the variety of cosmetic products. In the conventional zeolite-based cosmetics, the discharging rate of the antibacterial ions are determined by the ion concentration equilibrium regarding said chemical ion exchange reaction, so that it is almost impossible to control the discharging rate with adjusting the size or the composition of the zeolite particles.

The soluble glass is pulverized into particles. The average particle size is preferably set in a range of less than 20 µm.

When the average particle size exceeds 20 μm, the glass particles become too coarse to achieve a comfortable fitting to a human skin. The average particle size is preferably set in a range of less than 10 μm, and further more preferably in a range of less than 5 μm or less.

For aforementioned phosphate glass, CaO and MgO components can be blended separately or simultaneously. In the case of separate blending, the glass containing MgO tends to exhibit a lower solubility than that containing the same mole fraction of CaO. This means that using MgO is advantageous for preparing cosmetics containing very fine glass particles because the glass particles become more water-resistive. Specifically, the content of MgO in the soluble glass is preferably set in a range of 37–47 mol %, and the average particle size is preferably set to be 1 μm or less. Such mode are particularly suitable for cosmetics, which contains more than 70 wt % of water in the recipe thereof, and wherein the cosmetic base comprises a liquid material selected from the group consisting of skin lotion, milky lotion, shampoo and hair rinse. In this case, the soluble glass particles may be suspended in the liquid cosmetic base.

The rate of eluting of said antibacterial metal ions in water from the soluble glass is preferably set in a range of 0.00001–0.1 mg per hour per gram of said soluble glass on the condition that the soluble glass has a particle size of 420–600 μm and the water has a temperature of 20° C. If the eluting rate is set to be less than 0.00001 mg per hour per gram, the antibacterial effect may become insufficient. On the other hand, an eluting rate exceeding 0.1 mg per hour per gram may make the duration of the antibacterial effect too short. A more preferable range is 0.0001–0.01 mg per hour per gram of said soluble glass on the condition that the soluble glass has a particle size of 420–600 μm and the water has a temperature of 20° C.

DETAILED DESCRIPTION OF THE PREFERRED EMBODIMENTS

Several examples of this invention will now be described.

(EXAMPLE 1)

A soluble glass containing $Ag^+$ was prepared through the following procedure: 48 parts (in mol) of diphosphorous pentaoxide ($P_2O_5$), 42 parts of calcium oxide (CaO) and 10 parts of aluminium oxide ($Al_2O_3$) and 0.5 parts (in weight) of silver oxide ($Ag_2O$) were weighed and sufficiently mixed. The mixture was heated at 1300° C. for 8–10 hr to form a molten glass. After cooling, the soluble glass was pulverized in a ball mill to form 2 μm average sized particle. The particle size was measured using a laser forward scattering method (the same in the following example).

Components 1 and 2 described below were prepared respectively, and the Component 1 was molten at a designated temperature. Then the Component 1 was gradually emulsified into the Component 2 which had been preliminarily mixed thoroughly, thereby forming a soluble glass-based milky lotion. The Component 2 was prepared for two types, i.e., one of which contains 0.2 wt % of KOH, and the other of which contains no KOH.

| Component 1: | |
|---|---|
| Stearic acid | 2 parts |
| Vaseline | 5 parts |
| Liquid paraffin | 11 parts |
| Polyoxyethylene monooleate | 4 parts |
| Component 2: | |
| Polyoxyethylene glycol | 3 parts |
| Acrylic resin-coated titanium dioxide particles (containing 30% of acrylic resin) | 1 parts |
| Silver-containing soluble glass | 0.5 parts |
| Distilled water | 73.5 parts |

A zeolite-based milky lotion was prepared using the following procedure: Y-type zeolite particles ($1.14Na_2O.Al_2O_3.4.9SiO_2.xH_2O$, average particle size 2.0 μm) were immersed in an aqueous solution of 10 mol % of $AgNO_3$, and then rinsed in water and subsequently dried. The $Ag^+$ content supported on the particles was 3 wt %. A milky lotion was then prepared by using the zeolite particles instead of the soluble glass particles in the Component 2 according to a similar procedure.

As the first experiment, each milky lotions obtained were preserved in bottles for 6 month at ambient temperature in a dark place while the bottles were periodically opened once (for 10 minutes) per day, and after that, the solid component was filtered by a membrane filter from the lotions, and the $Ag^+$ concentration was measured by using atomic absorption spectrochemical analysis for the residual liquids, respectively.

For the lotion using Component 2 containing no KOH, the resulting $Ag^+$ concentration were 0.025 μg/g for the soluble glass-based lotion and 0.004 μg/g for the zeolite-based lotion. The liquid cosmetic base contains no alkaline-metal ion source, so that the eluting amount of $Ag^+$ is very small for zeolite-based lotion, while the soluble glass-based lotion exhibited a value preferable for maintaining an antibacterial effect. On the other hand, for the lotion using Component 2 containing KOH, the $Ag^+$ concentration for the zeolite-based lotion increased drastically to 0.045 μg/g, while that for soluble glass-based lotion exhibited almost the same value.

As the second experiment, 0.1 g of the soluble glass-based and zeolite-based milky lotions (using Component 2 without containing KOH) obtained were added to 300 ml of physiological brine and held statically for 1 hr, respectively. Then, the soluble glass and zeolite particles in the brine were filtered by a membrane filter, and the $Ag^+$ concentration was measured for the residual brine. The resulting value of $Ag^+$ concentration was 0.001 μg/g for the soluble glass-based lotion and 14.5 μg/g for the zeolite-based lotion. The high $Ag^+$ concentration for the zeolite-based lotion appears tribe due to the drastic chemical ion exchange reaction between $Na^+$ and $Ag^+$ ions. On the other hand, in the soluble glass-bases lotion, the $Ag^+$ ions elute gradually along with the physical dissolution of soluble glass particles, so that the measured $Ag^+$ concentration shows much smaller value than that for zeolite-based lotion.

(EXAMPLE 2)

A soluble glass containing $Ag^+$ was prepared through the following procedure: 50 parts (in mol) of diphosphorous pentaoxide ($P_2O_5$), 44 parts of magnesium oxide (MgO) and 6 parts of aluminium oxide ($Al_2O_3$) and 1 parts (in weight) of silver oxide ($Ag_2O$) were weighed and sufficiently mixed. The mixture was heated at 1300° C. for 8–10 hr to form a molten glass. After cooling, the soluble glass was pulverized in a ball mill to form 0.5 μm average sized particle.

Components 1 and 2 described below were prepared respectively, and the Component 1 was molten at a designated temperature. Then the Component 1 was gradually emulsified into the Component 2 which had been preliminarily mixed thoroughly, thereby forming a soluble glass-based lotion. The Component 2 was prepared for two types, i.e., one of which contains 0.2 wt % of KOH, and the other of which contains no KOH.

| Component 1: | |
| --- | --- |
| Acrylic resin-coated zinc oxide particles (containing 50% of acrylic resin) | 9 parts |
| Stearic acid | 1 parts |
| Dimethyl polysiloxane | 5 parts |
| Glycerol monostearate | 2 parts |
| Perfume | 0.1 parts |
| Component 2: | |
| Glycerol | 10 parts |
| Silver-containing soluble glass | 0.5 parts |
| Distilled water | 72.2 parts |

A zeolite-based lotion was prepared using the following procedure: Y-type zeolite particles ($1.14Na_2O.Al_2O_3.4.9SiO_2.xH_2O$, average particle size 0.5 μm) were immersed in an aqueous solution of 10 mol % of $AgNO_3$, and then rinsed in water and subsequently dried. The $Ag^+$ content supported on the particles was 3 wt %. A lotion was then prepared by using the zeolite particles instead of the soluble glass particles as contained in the Component 2 according to a similar procedure.

The first experiment was performed following the same procedure as that for Example 1. For the lotion using Component 2 containing no KOH, the resulting $Ag^+$ concentration were 0.008 μg/g for the soluble glass-based lotion and 0.002 μg/g for the zeolite-based lotion. On the other hand, for the lotion using Component 2 containing KOH, the $Ag^+$ concentration for the zeolite-based lotion increased drastically to 0.040 μg/g while that for soluble glass-based lotion exhibited almost the same value.

The second experiment was also performed following the same procedure as that for Example 1. The resulting value of $Ag^+$ concentration was 0.001 μg/g for the soluble glass-based lotion and 14.0 μg/g for the zeolite-based lotion.

Furthermore, as the third experiment, the soluble glass-based and zeolite-based lotions (using Component 2 containing KOH) were preserved for 6 month in colorless and transparent bottles, respectively, under exposure to light. The soluble glass-based lotion showed no change in appearance, but the zeolite-based lotion slightly turned black.

(EXAMPLE 3)

A soluble glass containing $Ag^+$ was prepared through the following procedure: 92 parts (in weight) of magnesium hydropyrophosphate ($MgH_2P_2O_7$), 15.3 parts of aluminum phosphate ($AlPO_4$) and 1.47 parts of silver nitrate ($AgNO_3$) were weighed and sufficiently mixed. The mixture was heated at 1300° C. for 8–10 hr to form a molten glass. After cooling, the soluble glass obtained (chemical composition: $P_2O_5$=50 mol %, MgO=44 mol %, $Al_2O_3$=6 mol %, $Ag_2O$= 1.0 wt %) was pulverized in a ball mill to form 2 μm average sized particle.

Components 1–5 are described below. First, the Components 1 and 2 were mixed together in a Henschel type mixer, and then the Component 3 was sprayed onto the mixture of Components 1 and 2 under continuous mixing. The resultant mixture was crushed using an atomizer and then mixed with the Component 4. Finally, Component 5 was sufficiently dissolved into the resulting mixture, thereby forming a soluble glass-based liquid foundation. The Component 4 was prepared for two types, i.e, one of which contains 0.2 wt % of KOH, and the other of which contains no KOH.

| Component 1: | |
| --- | --- |
| Titanium dioxide | 3 parts |
| Zinc oxide | 5 parts |
| Mica | 10 parts |
| Talc | 10 parts |
| Iron oxide red | 0.7 parts |
| Iron oxide yellow | 1.1 parts |
| Iron oxide black | 0.2 parts |
| Component 2: | |
| Soluble glass particles prepared in the step (1) = | 0.5 parts |
| Component 3: | |
| Squalane | 10 parts |
| Component 4: | |
| Glycerine | 1 parts |
| Distilled water | 48.5 parts |
| Component 5: | |
| Ethanol | 10 parts |

A zeolite-based liquid foundation was prepared using the following procedure: Y-type zeolite particles ($1.14Na_2O.Al_2O_3.4.9SiO_2.xH_2O$, average particle size 2.0 μm) were immersed in an aqueous solution of 10 mol % of $AgNO_3$, and then rinsed in water and subsequently dried. The $Ag^+$ content supported on the particles was 3 wt %. A liquid foundation was then prepared by using the zeolite particles instead of the soluble glass particles as the Component 2 according to a similar procedure.

The first experiment was performed following the same procedure as that for Example 1. For the liquid foundation using Component 4 containing no KOH, the resulting $Ag^+$ concentration were 0.008 μg/g for the soluble glass-based one and 0.001 μg/g for the zeolite-based one. On the other hand, for the liquid foundation using Component 4 containing KOH, the $Ag^+$ concentration for the zeolite-based one increased drastically to 0.038 μg/g while that for soluble glass-based one exhibited almost the same value.

The second experiment was also performed following the same procedure as that for Example 1. The resulting value $Ag^+$ concentration was 0.001 μg/g for the soluble glass-based one and 13.8 μg/g for the zeolite-based one.

(EXAMPLE 4)

A soluble glass containing $Ag^+$ was prepared through the following procedure: 20 parts (in mol) of boric acid ($B_2O_3$), 50 parts of silicon dioxide ($SiO_2$) and 30 parts of sodium oxide ($Na_2O$) and 0.5 parts (in weight) of silver oxide ($Ag_2O$) were weighed and sufficiently mixed. The mixture was heated at 1300° C. for 8–10 hr to form a molten glass.

After cooling, the soluble glass was pulverized in a ball mill to form 2 μm average sized particle.

By using following Components 1–5, a soluble glass-based liquid foundation was prepared according to the same procedure as that for example 2. The Component 5 was prepared for two types, i.e. one of which contains 0.2 wt % of KOH, and the other of which contains no KOH.

| Component 1: | |
|---|---|
| Titanium dioxide | 2.5 parts |
| Zinc oxide | 3.5 parts |
| Mica | 10 parts |
| Talc | 10 parts |
| Iron oxide red | 1 parts |
| Silica | 5 parts |
| Component 2: | |
| Soluble glass particles prepared in the step (1) = | 0.5 parts |
| Component 3: | |
| Stearic acid | 4 parts |
| Component 4: | |
| Butylene glycol | 10 parts |
| Component 5: | |
| Distilled water | 53.5 parts |

On the other hand, the same zeolite-based liquid foundation as that for example 2 was prepared as a reference sample.

The first experiment was performed following the same procedure as that for Example 1. For the liquid foundation using Component 5 containing no KOH, the resulting $Ag^+$ concentration were 0.018 μg/g for the soluble glass-based one and 0.001 μg/g for the zeolite-based one. In the other hand, for the liquid foundation using Component 5 containing KOH, the $Ag^+$ concentration for the zeolite-based one increased drastically to 0.055 μg/g while that for soluble glass-based one exhibited almost the same value.

The second experiment was also performed following the same procedure as that for Example 1. The resulting value $Ag^+$ concentration was 0.001 μg/g for the soluble glass-based one and 14.3 μg/g for the zeolite-based one.

(EXAMPLE 5)

A liquid foundation composed of the following Components 1 to 5 was prepared.

| Component 1 | |
|---|---|
| Titanium dioxide | 3 parts |
| Zinc oxide | 5 parts |
| Mica | 10 parts |
| Talc | 10 parts |
| Iron oxide red | 0.7 parts |
| Iron oxide yellow | 1.1 parts |
| Iron oxide black | 0.2 parts |
| Component 2 | |
| Silver-containing soluble glass | 0.5 parts |
| Component 3 | |
| Squalane | 10 parts |
| Component 4 | |
| Ethyl alcohol | 10 parts |

| Component 5 | |
|---|---|
| Glycerol | 1 parts |
| Distilled water | 48.5 parts |

The silver ion containing soluble glass of the Component 2 has the following conditions;

Theoretical glass composition:
  $P_2O_5$ 50 mol %; MgO 44 mol %; $Al_2O_3$ 6 mol %; $Ag_2O$ 1.0 wt %;

Dissolving speed:
  0.0003 mg/g/Hr (silver ion eluting amount in water at 20° C. in a glass particle size of 425–600 μm);

Particle size: 5 μm or less.

The Components 1 and 2 were mixed together by using a Henschel mixer, and the Component 3 was sprayed to the mixture thus obtained to carry 6out further mixing. Then, the mixture was pulverized by using an atomizer.

The Component 4 was added to the Component 5 to carry out sufficient mixing. Then, the mixture of the Components 1, 2 and 3 was added to the mixture of the Components 4 and 5 to carry out uniform mixing, thereby obtaining the objective liquid foundation.

The talc used was unsterilized, and a standard plate count of bacteria and a mold count of the liquid foundation and the talc used were measured. The results of measurement are shown in Table 1.

TABLE 1

| | Standard plate count of bacteria | Mold count |
|---|---|---|
| Liquid foundation | Negative/g | Negative/g |
| Talc | 500/g | 200/g |

This liquid foundation was used with a puff twice a day under an ordinary condition, and the standard plate count of bacteria and the mold count were measured after six months. As the result, both the standard plate count and the mold count of the liquid foundation in Example 5 were negative, and no problems occurred.

(EXAMPLE 6)

A liquid foundation composed of the following Components 1 to 5 was prepared.

| Component 1 | |
|---|---|
| Titanium dioxide | 3 parts |
| Zinc oxide | 5 parts |
| Mica | 10 parts |
| Talc | 8 parts |
| Iron oxide red | 0.7 parts |
| Iron oxide yellow | 1.1 parts |
| Iron oxide black | 0.2 parts |
| Component 2 | |
| Copper-containing soluble glass | 2.5 parts |
| Component 3 | |
| Squalane | 10 parts |
| Component 4 | |
| Ethyl alcohol | 10 parts |

-continued

| Component 5 | |
|---|---|
| Glycerol | 1 parts |
| Distilled water | 48.5 parts |

The copper ion containing soluble glass of the Component 2 has the following conditions;
Theoretical glass composition:
$P_2O_5$ 50 mol %; $K_2O$ 20 mol %; CaO 15 mol %; CuO 5.0 mol %;
Dissolving speed:
0.002 mg/g/Hr (copper ion eluting amount in water at 20° C. in a glass particle size of 425–600 μm);
Particle size: 10 μm or less.

The Components 1 and 2 were mixed together by using a Henschel mixer, and the Component 3 was sprayed to the mixture thus obtained to carry out further mixing. Then, the mixture was pulverized by using an atomizer.

The Component 4 was added to the Component 5 to carry out sufficient mixing. Then, the mixture of the Components 1, 2 and 3 was added to the mixture of the Components 4 and 5 to carry out uniform mixing, thereby obtaining the objective liquid foundation.

The talc used was unsterilized, and a standard plate count of bacteria and a mold count of the liquid foundation and the talc used were measured. The results of measurement are shown in Table 2.

TABLE 2

| | Standard plate count of bacteria | Mold count |
|---|---|---|
| Liquid foundation | Negative/g | Negative/g |
| Talc | 500/g | 200/g |

This liquid foundation was used with a puff twice a day under an ordinary condition, and the standard plate count of bacteria and the mold count were measured after six months. As the result, both the standard plate count and the mold count of the liquid foundation in Example 6 were negative, and no problems occurred.

What is claimed is:

1. Cosmetic products containing a soluble glass, comprising soluble glass particles and liquid cosmetic base containing water, wherein said soluble glass contains antibacterial metal ions selected from the group consisting of $Ag^+$, $Cu^+$, $Cu^{2+}$ and $Zn^{2+}$, and having a rate of eluting of said antibacterial metal ions in water from about 0.00001–0.1 mg per hour per gram of said soluble glass on the condition that the soluble glass has a particle size of 420–600 μm and the water has a temperature of 200° C., and wherein said antibacterial metal ions elute from said soluble glass particles with the dissolution of said soluble glass into water.

2. Cosmetic products as defined in claim 1, wherein said cosmetic base comprises a liquid material selected from the group consisting of liquid foundation, skin lotion, milky lotion, shampoo, hair rinse and cream.

3. Cosmetic products as defined in claim 2 which contains more than 40 wt % of water in the recipe thereof.

4. Cosmetic products as defined in claim 1, wherein said antibacterial metal ions are $Ag^+$.

5. Cosmetic products as defined in claim 4, wherein said soluble glass contains $B_2O_3$, $SiO_2$, $Na_2O$ and $Ag_2O$.

6. Cosmetic products as defined in claim 5, wherein said soluble glass contains 10–30 mol % of $B_2O_3$, 40–60 mol % of $SiO_2$, 20–40 mol % of $Na_2O$ and 0.1–12 wt % of $Ag_2O$.

7. Cosmetic products as defined in claim 5, wherein said soluble glass contains 15–25 mol % of $B_2O_3$, 45–55 mol % of $SiO_2$, 25–35 mol % of $Na_2O$ and 0.1–2 wt % of $Ag_2O$.

8. Cosmetic products as defined in claim 4, wherein said soluble glass contains $P_2O_5$, at least one of CaO and MgO, $Al_2O_3$ and $Ag_2O$.

9. Cosmetic products as defined in claim 8, wherein said soluble glass contains 38–58 mol % of $P_2O_5$, 32–52 mol % of at least one of CaO and MgO in total, 6–14 mol % of $Al_2O_3$ and 0.1–2 wt % of $Ag_2O$.

10. Cosmetic products as defined in claim 8, wherein said soluble glass contains 43–53 mol % of $P_2O_5$, 37–47 mol % of at least one of CaO and MgO in total, 8–12 mol % of $Al_2O$ and 0.1–2 wt % of $Ag_2O$.

11. Cosmetic products as defined in claim 9, wherein said soluble glass contains 37–47 mol % of MgO,
and wherein said soluble glass particles have an average particle size of 1 μm or less.

12. Cosmetic products as defined in claim 11, which contains more than 70 wt % of water in the recipe thereof;
and wherein said cosmetic base comprises a liquid material selected from the group consisting of skin lotion, milky lotion, shampoo and hair rinse.

13. Cosmetic products as defined in claim 1, wherein said soluble glass particles have an average particle size of 20 μm or less.

14. Cosmetic products as defined in claim 1, wherein said soluble glass particles have an average particle size of 10 μm or less.

15. Cosmetic products as defined in claim 1, said soluble glass comprising antibacterial metal ions selected from the group consisting of $Ag^+$, $Cu^+$, $Cu^{2+}$ and $Zn^{2+}$, and having a rate of eluting of said antibacterial metal ions in water from about 0.0001–0.01 mg per hour per gram of said soluble glass on the condition that the soluble glass has a particle size of 42014 600 μm and the water has a temperature of 20° C.

16. Cosmetic products as defined in claim 1 comprising said soluble glass particles having an average particle size of 20 μm or less, said soluble glass comprising $P_2O_5$, MgO, $Al_2O_3$ and $Ag_2O$, having a rate of eluting of $Ag^+$ ions in water from about 0.00001– 0.1 mg per hour per gram of said soluble glass on the condition that the soluble glass has a particle size of 420–600 μm and the water has a temperature of 20° C., wherein said metal ion elutes from said soluble glass with the dissolution of said soluble glass into water, and wherein said cosmetic base comprises a liquid material selected from the group consisting of liquid foundation, skin lotion, milky lotion, shampoo, hair rinse and cream.

17. Cosmetic products as defined in claim 1 comprising said soluble glass particles having an average particle size of 10 μm or less, said soluble glass comprising $P_2O_5$, MgO, $Al_2O_3$ and $Ag_2O$, having a rate of eluting of $Ag^+$ ions in water from about 0.0001–0.01 mg per hour per gram of said soluble glass on the condition that the soluble glass has a particle size of 420–600 μm and the water has a temperatures of 20° C., wherein said metal ion elutes from said soluble glass with the dissolution of said soluble glass into water, and wherein said cosmetic base comprises a liquid material selected from the group consisting of liquid foundation, skin lotion, milky lotion, shampoo, hair rinse and cream.

18. Cosmetic products as defined in claim 1 comprising said soluble glass particles having an average particle size of 20 μm or less, said soluble glass comprising $B_2O_3$, $SiO_2$, $Na_2O$ and $Ag_2O$, having a rate of eluting of $Ag^+$ ions in water from about 0.00001–0.1 mg per hour per gram of said soluble glass on the condition that the soluble glass has a particle size of 420–600 μm and the water has a temperature of 20° C., wherein said metal ion elutes from said soluble glass with the dissolution of said soluble glass into water, and wherein said cosmetic base comprises a liquid material selected from the group consisting of liquid foundation, skin lotion, milky lotion, shampoo, hair rinse and cream.

19. Cosmetic products as defined in claim 1 comprising said soluble glass particles having an average particle size of 10 μm or less, said soluble glass comprising $B_2O_3$, $SiO_2$, $Na_2O$ and $Ag_2O$ having a rate of eluting of $Ag^+$ ions in water from about 0.0001–0.01 mg per hour per gram of said soluble glass on the condition that the soluble glass has a particle size of 420–600 μm and the water has a temperature of 20° C., wherein said metal ion elutes from said soluble glass with the dissolution of said soluble glass into water, and wherein said cosmetic base comprises a liquid material selected from the group consisting of liquid foundation, skin lotion, milky lotion, shampoo, hair rinse and cream.

* * * * *